US00PP12499P2

(12) United States Plant Patent
Meilland

(10) Patent No.: US PP12,499 P2
(45) Date of Patent: Mar. 26, 2002

(54) HYBRID TEA ROSE PLANT NAMED 'MEILEYET'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/276,713

(22) Filed: Mar. 26, 1999

(51) Int. Cl.[7] ..... A01H 5/00
(52) U.S. Cl. ..... Plt./137
(58) Field of Search ..... Plt./130, 133, 134, Plt./132, 137

(56) References Cited

PUBLICATIONS

UPOV–ROM, 2000/06, Plant Variety Database, GTI Jouve Retrieval Software, citation for 'Meileyet'.*

Protection Des Obtentions Vegetales, Bulletin Officiel du Comité de la Protection des Obtentions Végétales, Cover Page and pp. 475, 480, 481 and 485 (Oct. 1997).

Protection Des Obtentions Vegetales, Bulletin Officiel du Comité de la Protection des Obtentions Végétales, Cover Page and pp. 109 and 115 (Mar. 1999).

* cited by examiner

*Primary Examiner*—Howard J. Locker
(74) *Attorney, Agent, or Firm*—Burns, Doane, Swecker & Mathis, L.L.P.

(57) ABSTRACT

A new and distinct variety of Hybrid Tea rose plant is provided which forms attractive double blossoms that are pale pink bordered with pink depending on the season. Such blossoms possess no fragrance. The plant exhibits an erect growth habit, dark green and semi-glossy foliage, and very good disease resistance. The new variety is particularly well suited for producing cut flowers under greenhouse growing conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Tanselbon' variety (non-patented in the United States). The male parent (i.e., the pollen parent) was the product of the cross of the 'Erotika' variety (non-patented in the United States) and the 'Devolor' variety (non-patented in the United States). The parentage of the new variety can be summarized as follows:

'Tanselbon'×('Erotika'×'Devolor').

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) Is substantially free of thorns,
(b) Forms attractive double blossoms that are pale pink bordered with pink depending on the season,
(c) Exhibits an erect growth habit, and
(d) Is particularly well suited for the production of cut flowers under greenhouse growing conditions.

The new variety well meets the needs of the horticultural industry and exhibits good productivity during cut flower production in a greenhouse.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meileyet' variety.

BRIEF DESCRIPTION OF THE PHOTOGRAPH

The accompanying photograph shows as nearly true as it is reasonably possible to make the same in a color illustration of this character, typical specimens of the plant parts of the new variety. The rose plants of the new variety were two years of age and were observed during April while budded on *Rosa indica* understock and growing in greenhouses at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface; and FIG. 15—illustrates a specimen of a leaf with five leaflets—plan view—under surface.

DETAILED DESCRIPTION

The chart used in the identification of the colors is that of The Royal Horticultural Society (R.H.S. Colour Chart). The description is based on the observation of two year-old plants during April while budded on *Rosa indica* understock and growing indoors at Le Cannet des Maures, Var, France. The coloration in common terms precedes reference to the chart in some instances.

Class: Hybrid tea.

Plant:

*Height.*—When pruned to a height of 85 cm., floral stems of approximately 60 to 80 cm. in length commonly are produced.

*Habit.*—Erect.

Branches:

*Color.*—Young stems: near Green Group 137D. Adult wood: near Green Group 137C.

*Thorns.*—Size: medium when present. Quantity: very few, is substantially free of thorns. Color: greenish. Configuration: fairly straight and fringed on the upper surface and slightly curved on the under surface.

Leaves:

*Stipules.*—Adnate, pectinate, and narrow.

*Petioles.*—Upper surface: slightly glandular, and medium green in coloration. Under surface: commonly with a few prickles and light green (near Green Group 137A) in coloration suffused with anthocyanin coloration.

*Leaflets.*—Number: 3, 5 (most often), and 7. Shape: with a symmetrical tip. Serration: regular (as illustrated). Texture: normal. General appearance: fairly dense, medium green, and semi-glossy. Color (young foliage): Upper surface: near Green Group 137A with some reddish staining. Under surface: near Greyed-Green Group 191A with some reddish staining. Color (adult foliage): Upper surface: near Yellow-Green Group 147A. Under surface: near Greyed-Green Group 191A.

Inflorescence:

*Number of flowers.*—Usually one flower per stem.

*Peduncle.*—Long, without prickles, light green (near Green Group 137D) in coloration, and the length is approximately 14 cm. on average.

*Sepals.*—Upper surface: tomentose and light green (near Green Group 137D) in coloration. Under surface: light green (near Green Group 137D) in coloration and commonly with extensions of variable lengths (as illustrated).

*Buds.*—Shape: conical. Size: medium. Length: approximately 5 cm. on average. Color upon opening: Upper surface: near Yellow-White Group 158D suffused with Red Group 55D at the margin. Under surface: near Yellow-White Group 158C suffused with Red Group 55B to 55C.

*Flower.*—Shape: with a high center. Size: large. Diameter: commonly approximately 12 cm. on average. Color (when opening begins): Upper surface: other than the outermost petals pale pink, Orange Group 27C to 27D and lightly suffused with Red Group 56D at the margin depending on the season. The outermost petals approach white, White Group 155B, in coloration. Under surface: near White Group 155A and suffused with Red Group 55D at the margin. Color (when blooming): Upper surface: other than the outermost petals pale pink, Orange Group 27C to 27D and suffused with light pink, Red Group 56D, at the margin depending upon the season. The outermost petals approach white, White Group 155B, in coloration. Under surface: White Group 155A suffused with Red Group 55D at the margin. Color (at end of opening): Upper surface: other than the outermost petals pale pink, Orange Group 27C to 27D. The outermost petals approach white, White Group 155B, in coloration. Under surface: near White Group 155C with a slight presence of Red Group 55D at the margin. Fragrance: none. Lasting quality: approximately 10 to 12 days on the plant and approximately 10 to 12 days when cut and placed in a vase. Petal shape: cuneiform base and reflexed tip. Petal number: approximately 55 on average. Petal drop: very good, the petals commonly detach cleanly. Stamen number: approximately 45 on average. Anthers: yellow in coloration. Filaments: yellow in coloration. Pistils: approximately 140 on average. Stigmas: pale yellow in coloration. Styles: pinkish in coloration. Receptacle: light green in coloration, and in longitudinal section in the shape of a funnel. Hips: ovoid in shape.

Development:

*Vegetation.*—Very strong.

*Blooming.*—Early and abundant, approximately 140 to 180 blossoms are formed per square meter per year under greenhouse growing conditions.

*Aptitude to bear fruit.*—Medium.

*Resistance to diseases.*—Very good with respect to Powdery Mildew.

I claim:

1. A new and distinct variety of Hybrid Tea rose plant characterized by the following combination of characteristics:

(a) Is substantially free of thorns,
(b) Forms attractive double blossoms that are pale pink bordered with pink depending on the season,
(c) Exhibits an erect growth habit, and
(d) Is particularly well suited for the production of cut flowers under greenhouse growing conditions;

substantially as herein shown and described.

* * * * *

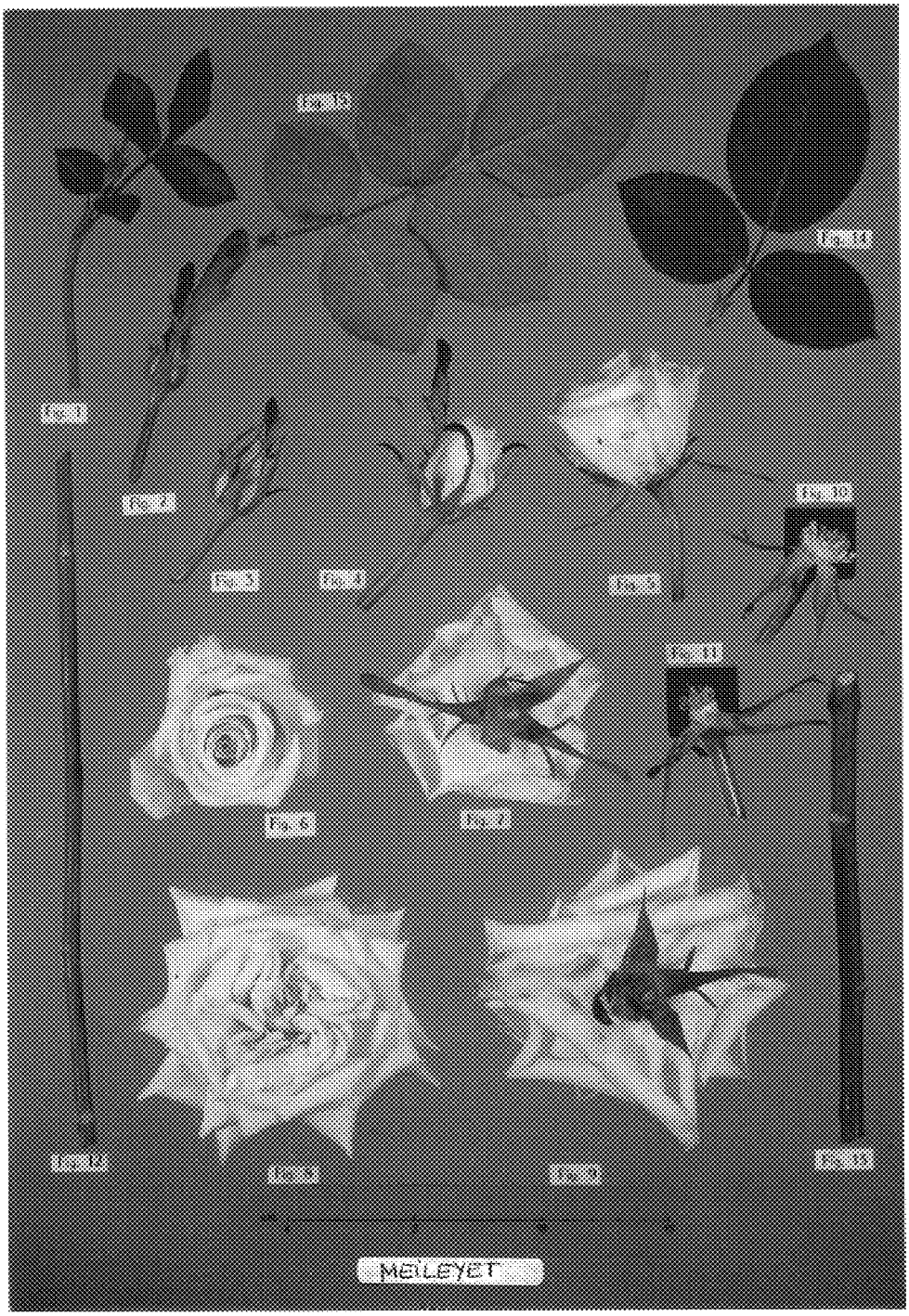
MALLEYET